(12) United States Patent  
Kuroda

(10) Patent No.: US 12,085,502 B2
(45) Date of Patent: Sep. 10, 2024

(54) SUBSTRATE FOR UV TRANSMITTANCE EVALUATION OF COSMETICS AND EVALUATION METHOD

(71) Applicants: KURODA CONSULTING INCORPORATED, Yokohama (JP); NIKKO CHEMICALS CO., LTD., Tokyo (JP); COSMOS TECHNICAL CENTER CO., LTD., Tokyo (JP)

(72) Inventor: Akihiro Kuroda, Yokohama (JP)

(73) Assignees: KURODA CONSULTING INCORPORATED, Yokohama (JP); NIKKO CHEMICALS CO., LTD., Tokyo (JP); COSMOS TECHNICAL CENTER CO., LTD., Tokyo (JP)

( * ) Notice: Subject to any disclaimer, the term of this patent is extended or adjusted under 35 U.S.C. 154(b) by 286 days.

(21) Appl. No.: 17/621,655

(22) PCT Filed: Jul. 29, 2020

(86) PCT No.: PCT/JP2020/029011
§ 371 (c)(1),
(2) Date: Dec. 21, 2021

(87) PCT Pub. No.: WO2021/020432
PCT Pub. Date: Feb. 4, 2021

(65) Prior Publication Data
US 2022/0349816 A1     Nov. 3, 2022

(30) Foreign Application Priority Data
Jul. 31, 2019    (JP) .................................. 2019-141652

(51) Int. Cl.
*G01N 21/33* (2006.01)
*A61K 8/60* (2006.01)
*C03C 23/00* (2006.01)

(52) U.S. Cl.
CPC ............... *G01N 21/33* (2013.01); *A61K 8/60* (2013.01); *C03C 23/002* (2013.01)

(58) Field of Classification Search
CPC .................. G01N 21/33; G01N 33/15; G01N 2021/0339; A61K 8/60; C03C 23/002;
(Continued)

(56) References Cited

U.S. PATENT DOCUMENTS

2005/0069639 A1    3/2005   Ogata et al.
2005/0255526 A1   11/2005   Kanda et al.
(Continued)

FOREIGN PATENT DOCUMENTS

JP      S5692183 A      7/1981
JP    2002148403 A      5/2002
(Continued)

OTHER PUBLICATIONS

International Preliminary Report on Patentability, dated Feb. 1, 2022, for corresponding international application PCT/JP2020/029011 (1 page).
(Continued)

*Primary Examiner* — Md M Rahman
(74) *Attorney, Agent, or Firm* — Law Office of Katsuhiro Arai

(57) ABSTRACT

An object is to develop a measurement method, and a measurement substrate, for measuring SPF or other value in a single measurement, instead of having to measure it on many substrates as has been the case to date. As a solution, a substrate for UV transmittance evaluation, including a base material that allows UV rays in a range of 290 to 400 nm to transmit through, and a layer provided on one side thereof that contains at least one type of compound other than cellulose triacetate that has a sugar skeleton but is not a salt, is provided.

8 Claims, 2 Drawing Sheets

(58) Field of Classification Search
CPC ....... C03C 2218/31; C03C 3/06; C03C 17/32; C03C 23/006
USPC ........................................................ 356/432
See application file for complete search history.

(56) References Cited

U.S. PATENT DOCUMENTS

| | | | |
|---|---|---|---|
| 2012/0082855 A1* | 4/2012 | Ohta | ................. G02B 1/111 427/164 |
| 2012/0262651 A1* | 10/2012 | Takeda | ............. G02F 1/133514 349/96 |
| 2019/0285543 A1 | 9/2019 | Asakura et al. | |

FOREIGN PATENT DOCUMENTS

| | | | |
|---|---|---|---|
| JP | 2005326165 A | | 11/2005 |
| JP | 2014071007 A | * | 4/2014 |
| WO | 2014092054 A1 | | 6/2014 |
| WO | 2018047707 A1 | | 3/2018 |

OTHER PUBLICATIONS

Notification Concerning Transmittal of International Preliminary Report on Patentability, mailed Feb. 10, 2022, for corresponding international application PCT/JP2020/029011 (1 page).

Notification of Transmittal of Translation of the International Preliminary Report on Patentability, mailed Feb. 10, 2022, for corresponding international application PCT/JP2020/029011 (1 page).

Written Opinion of the International Searching Authority, mailed Oct. 20, 2020, for corresponding international application PCT/JP2020/029011 (3 page).

Extended European Search Report (EESR) dated Jun. 16, 2023, issued for European counterpart patent application No. EP20847012.0 (7 pages).

Asakura et al., Hydrophilicity of the Substrate Surface under the Applied Sunscreen Layer Changes in vitro UV Protection Efficacies, IFSCC Magazine 2, 2018, 53-57. (5 pages).

Asakura et al., Hydrophilicity of the Substrate Surface under the Applied Sunscreen Layer that Changes the UV Protection Efficiency, Lecture abstracts of the 81st research forum of SCCJ, Nov. 29, 2017, p. 103. (2 pages).

Colipa Guidelines, Method for in vitro Determination of UVA protection, Jun. 2009. (24 pages).

International Search Report (ISR) mailed Oct. 20, 2020, issued for International application No. PCT/JP2020/029011. (2 page).

ISO/TR 26369, Cosmetics—Sun protection test methods—Review and evaluation of methods to assess the photoprotection of sun protection products, Technical Report, Sep. 1, 2009. (40 pages).

Japan Cosmetic Industry Association, SPF measurement method standards by Japan Cosmetic Industry Association, Revised in 2007, Jul. 10, 2007. (Machine translation of pp. 4-12 is attached) (54 pages).

Japan Cosmetic Industry Association, UV-protective cosmetics and UV-protective effects, SPF and PA Labeling, Revised in 2003. (Machine translation of pp. 25-31 is attached) (75 pages).

Rohr et al., In vitro Sun Protection Factor: Still a Challenge with No Final Answer, Skin Pharmacology Physiology. , Mar. 9, 2010, 201-212, 23. (12 pages).

* cited by examiner

[FIG. 1]
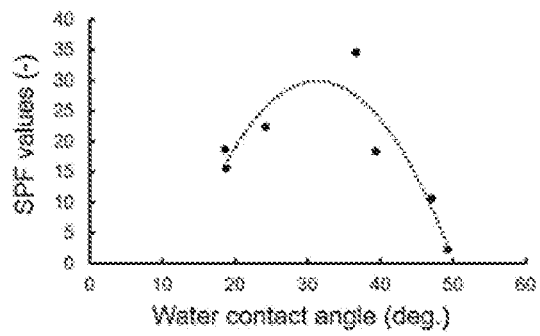
[FIG. 2]
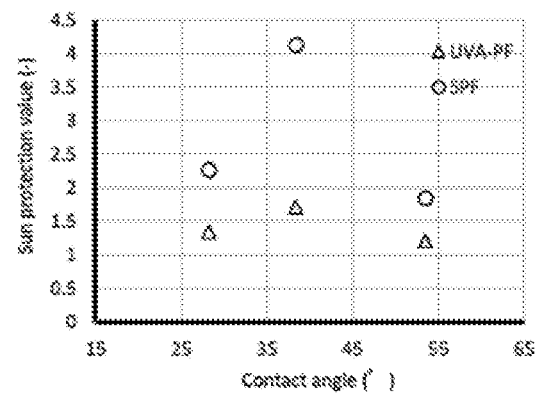
[FIG. 3]
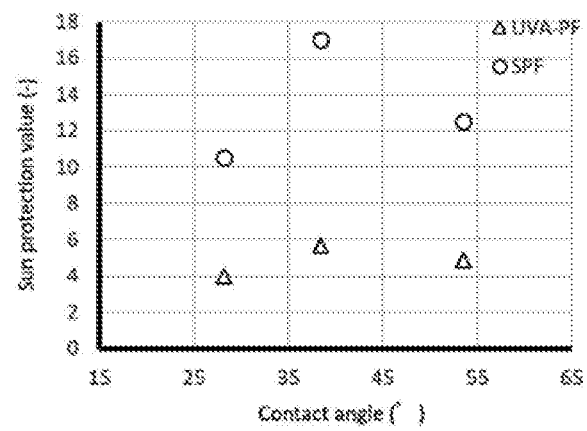

[FIG. 4]
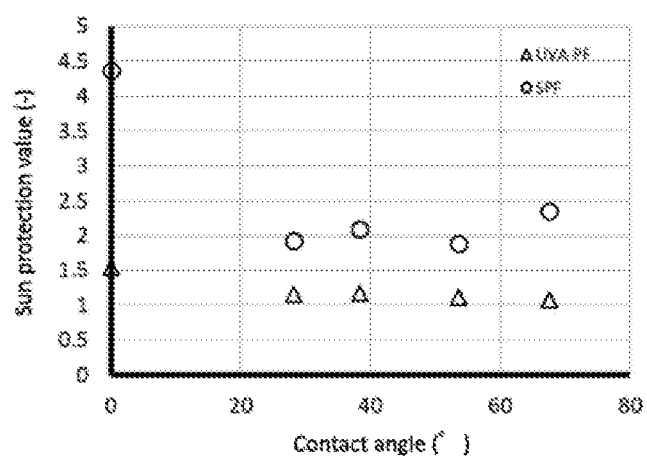

SUBSTRATE FOR UV TRANSMITTANCE EVALUATION OF COSMETICS AND EVALUATION METHOD

CROSS-REFERENCE TO RELATED APPLICATIONS

This application is the U.S. National Phase under 35 U.S.C. § 371 of International Application PCT/JP2020/029011, filed Jul. 29, 2020, which claims priority to Japanese Patent Application No. JP2019-141652, filed Jul. 31, 2019. The International Application was published under PCT Article 21(2) in a language other than English.

TECHNICAL FIELD

The present invention relates to a substrate for evaluating the UV protection performance of cosmetics, and a method for evaluation using the substrate.

BACKGROUND ART

The technical background of the present invention is explained below.

Currently in Japan, SPF (abbreviation for Sun Protection Factor) indicating the protection capability against B-wave UV rays of 290 to 320 nm in wavelength, and UVA-PA (Protection Grade of UVA) indicating the protection capability against A-wave UV rays of 320 to 400 nm in wavelength, are used as indicators of UV protection effects of cosmetics. To indicate the measured results of these on cosmetics, values measured according to the respective measurement methods and criteria specified by the Japan Cosmetic Industry Association (Non-patent Literature 1, Non-patent Literature 2), or grades thereof, must be indicated.

Overseas, it is also required that their indications basically follow the measurement methods and indication methods in their respective regions (Non-patent Literature 3); however, the basic measurement methods have mostly been standardized. Under these measurement methods and criteria, the backs of human subjects are used in such a way that high-output UV rays are irradiated on the backs and the inflammation reactions and pigmentation reactions occurring on the skins are visually observed, and the UV protection effects are measured based on the results. However, use of human subjects requires time/effort and money, and it also takes a long time before measured results can be obtained.

In addition, use of human subjects presents ethical as well as medical issues, etc., and therefore measurement methods that measure UV protection effects with machines, instead of using human subjects, are being studied in Japan and Europe (Non-patent Literature 4). However, reportedly the measurement methods currently under study present a number of problems (Non-patent Literature 5). A study conducted by the inventor of the present invention also found that the SPF values would vary by as much as 20-fold or so, even when the same sample was used and tested under the same standard.

This problem can be solved to a degree using the method in Patent Literature 1. However, a further study using this method revealed a new problem. It was the phenomenon of the sample producing significantly different measured values when substrates with different contact angles with water were used (Non-patent Literature 6).

Also, each cosmetic preparation varies in hydrophilicity and other physical properties based on its composition. When cosmetic preparations are applied on substrates whose contact angle with water is fixed, some cosmetic preparations may be applied uniformly, but others may not be applied uniformly and produce a nonuniform coating film as a result of the cosmetic preparation undergoing phase separation, or being repelled from parts of the substrate surface and thus causing the parts of the substrate surface to be exposed, etc.

This means that, even if the measurement accuracy is improved, the properties can be understood only after substrates having many different contact angles are prepared beforehand and then the values measured thereon are drawn into a graph; in other words, even the measurement of a single product possibly requires a lot of work, such as having to measure it on substrates having multiple different contact angles. Such time/effort is considerable compared to, and thus precludes any proposition that the aforementioned method would substitute, the in-vivo method.

In light of the above, a measurement method that would allow high-precision measurement with the least possible time/effort, had to be developed.

BACKGROUND ART LITERATURE

Patent Literature

Patent Literature 1: International Patent Laid-open No. 2018/047707

Non-Patent Literature

Non-patent Literature 1: Japan Cosmetic Industry Association; UV-Protective Cosmetics and UV-Protection Effects—SPF and PA Labeling —, Revised 2003.
Non-patent Literature 2: Japan Cosmetic Industry Association; SPF Measurement Method Standards by Japan Cosmetic Industry Association <Revised 2007>.
Non-patent Literature 3: ISO/TR26369 Cosmetics—Sun protection test methods—Review and evaluation of methods to assess the photoprotection of sun protection products.
Non-patent Literature 4: Colipa Guidelines, Method for In-vitro Determination of UVA Protection, 2009.
Non-patent Literature 5: Rohr, M., Klette, E., Ruppert, S., Bimzcok, R., Klebon, B., Heinrich, U., Tronnier, H., Johncock, W., Peters, S., Pfluecker, F., Rudolph, T., Floesser-Mueller, H., Jenni, K., Kockott, D., Lademann, J., Herzog, B., Bielfeldt, S., Mendrok-Edinger, C., Hanay, C., Zastrow, L. In-vitro Sun Protection Factor: Still a Challenge with No Final Answer, *Skin Pharmacol. Phys.*, 2010, 23(4), 201-212.
Non-patent Literature 6: Asakura, K., Kuroda, A. *IFSCC Magazine*, 21(2), 53-57 (2018).

SUMMARY OF THE INVENTION

Problems to be Solved by the Invention

An object of the present invention is to develop a measurement method, and a measurement substrate, for accurately evaluating (measuring) SPF or other value in a single measurement, instead of having to measure it on many substrates as has been the case to date, as described in Background Art above.

Means for Solving the Problems

Based on the relationship between the condition of a sample on a measurement substrate and its measured value, the measured SPF value becomes lower when the sample has undergone phase separation or the sample has been repelled from parts of the substrate surface and thus is partially absent on the substrate, while the measured value becomes higher when the sample covers the entire substrate uniformly in a stable manner without undergoing phase separation. This is one essence of the phenomenon that occurs when the contact angle of the substrate is changed.

This means that, by enabling automatic selection of the condition of coating film that represents the sample covering the entire substrate in a stable manner, and also by allowing this condition to be reproduced on the skin, such method would demonstrate excellent performance as an in-vivo substitute. Accordingly, the inventor of the present invention studied in earnest and eventually invented the measurement method and substrate for UV transmittance evaluation (hereinafter also referred to simply as "substrate") below:

1. A substrate for UV transmittance evaluation, comprising a base material that allows UV rays in a range of 290 to 400 nm to transmit through, and a layer provided on one side thereof that contains at least one type of compound other than cellulose triacetate that has a sugar skeleton but is not a salt.
2. The substrate for UV transmittance evaluation according to 1, whose contact angle with distilled water 5 minutes after it was dripped onto the layer that contains at least one type of compound other than cellulose triacetate that has a sugar skeleton but is not a salt, is different by 15 degrees or more from the contact angle immediately after dripping.
3. The substrate for UV transmittance evaluation according to 1 or 2, wherein the base material that allows UV rays in a range of 290 to 400 nm to transmit through is a quartz plate.
4. The substrate for UV transmittance evaluation according to any one of 1 to 3, wherein the compound that has a sugar skeleton but is not a salt is at least one type selected from mannose, galactose, xylose, glucose, maltose, lactose, sucrose, trehalose, fructose, cellulose, hydroxyethyl cellulose, hydroxypropyl cellulose, carboxymethyl cellulose, maltotriose, raffinose, inulin, oligosaccharide, glucan, agar, α-cyclodextrin, maltodextrin, cornstarch, powdered arrowroot, tapioca starch, potato starch, flour starch, hydroxyethyl starch, hydroxypropyl starch, Tamarind gum, xanthan gum, native gellan gum, and gellan gum.
5. A measurement method for SPF value, comprising steps A and B below:
A. coating a cosmetic preparation on the substrate for UV transmittance evaluation according to any one of 1 to 4; and
B. measuring the UV absorption spectrum that transmits through the coated substrate for UV transmittance evaluation, to obtain the transmittance and also obtain the SPF value.

Effects of the Invention

As explained above, implementing the measurement method proposed by the present invention using the substrate for UV transmittance evaluation proposed by the present invention has the effect of allowing accurate measured values to be obtained more easily for various types of cosmetic preparations using fewer measurement substrates.

BRIEF DESCRIPTION OF THE DRAWINGS

FIG. 1 Measured results of SPF in Example 1
FIG. 2 Figure showing the relationship between the contact angle of the substrate and the measured value of SPF
FIG. 3 Figure showing the relationship between the contact angle of the substrate and the measured value of SPF
FIG. 4 Measured results of SPF for cosmetic preparation 4

MODE FOR CARRYING OUT THE INVENTION

The present invention is explained in detail below.

The purpose of use of the substrate for UV transmittance evaluation and evaluation method proposed by the present invention is to primarily measure the transmittance of UV rays with respect to water-dispersible compositions and various other forms of cosmetic preparations of O/W emulsion type (oil-in-water type) including W/O/W type or of non-emulsion type.

(Cosmetic Preparations)

These cosmetic preparations include emulsified foundations and other makeup preparations, makeup bases, sunscreen creams, multi-layer separation type sunscreens, non-chemical sunscreens, day essences, day care lotions and other sun protection cosmetic preparations, etc. Also, types of formulations include liquid type, skin milk type, cream type, lotion type, essence type, multi-layer separation type, etc.

And, UV protection effects are obtained by applying these cosmetic preparations, etc., on the skin, or preferably on the face, body, arms, and legs, etc., whichever is applicable.

These UV protection effects, generally expressed by SPF values corresponding to B-wave UV rays of 290 to 320 nm in wavelength, UVA-PF values corresponding to A-wave UV rays of 320 to 400 nm in wavelength, or by PA ratings or PPD values, are not limited in any way so long as they conform to indicators indicating the protection effects against these wavelengths.

UV absorbents to be added to express UV absorption property are not limited in any way so long as those that can be added to cosmetics are used. Among these UV absorbents, oil-soluble ones include cinnamate-based UV absorbents, triazine-based UV absorbents, benzophenone-based UV absorbents, benzoate-based UV absorbents, salicylic acid-based UV absorbents, and dibenzoylmethane-based UV absorbents, and the like. Any one of these may be used alone, or two or more types may be combined.

Also, water-soluble ones including benzophenone-based UV absorbents, phenylbenzimidazole sulfonic acid, and/or 2-hydroxy-4-methoxybenzophenone sulfonic acid, etc., may be used.

Examples of pigments to be added to scatter and absorb UV rays include fine-grain titanium oxide, fine-grain zinc oxide, fine-grain cerium oxide, titanium oxide, zinc oxide, titania hydroxide sol, aluminum powder, gold leaf powder, methylene bis-benzotriazolyl tetramethylbutyl phenol, etc.

In addition, various types of components that can be compounded into cosmetic preparations, other than these UV absorbents and scattering agents, may be contained.

<Substrate for UV Transmittance Evaluation>

The substrate for UV transmittance evaluation proposed by the present invention comprises a base material that lets UV rays in a range of 290 to 400 nm transmit through, and a layer provided on one side thereof that contains a compound that has a sugar skeleton but is not a salt.

(Base Material that Lets UV Rays in a Range of 290 to 400 nm Transmit Through)

For the base material that is transparent to UV rays in a range of 290 to 400 nm and transmits these UV rays under the present invention, a quartz, glass, polymethyl methacrylate (PMMA), polyethyl terephthalate (PET), or other plate or sheet having smooth surface may be adopted, where a quartz plate is particularly preferred.

This base material needs only to have a so-called plate or sheet shape, but it must allow for measurement of transmitted UV rays in a range of 290 to 400 nm when made into a substrate for UV transmittance evaluation. The base material must let UV rays transmit through it fully, and also have necessary strength.

So that a uniform layer containing at least one type of compound other than cellulose triacetate that has a sugar skeleton but is not a salt as described below (hereinafter also referred to as "compound that has a sugar skeleton but is not a salt") will be formed on one side of the base material, the one side must have sufficiently high hydrophilicity. In other words, its water contact angle must be sufficiently small, and to this end, hydrophilization treatment for improving hydrophilicity may be performed beforehand as necessary. It should be noted that a "uniform layer" means the thickness of the layer is uniform and the surface of the layer is smooth.

This hydrophilization treatment takes the form of plasma treatment, arc discharge treatment, corona discharge treatment, or other treatment by physical means, which is performed on at least one side (surface on the side on which the cosmetic preparation to be measured is applied) of the aforementioned base material to bring the contact angle with pure water into a range of 0 to 20°, or preferably 0 to 10°, or more preferably 0 to 5°.

The conditions for these treatments, or specifically the applied voltage, treatment time, etc., may be determined as desired according to the intended contact angle. Also, regarding the atmosphere, corona discharge treatment may be performed in air, or plasma discharge treatment may be performed in vacuum or in an oxygen or argon atmosphere. For example, preferably a quartz substrate is treated with corona discharge.

(Layer Containing a Compound that has a Sugar Skeleton but is not a Salt)

After hydrophilization treatment is performed as described above on the base material as necessary, a layer containing a compound that has a sugar skeleton but is not a salt is formed on the hydrophilization-treated side.

The purpose of forming this layer is to change the water contact angle, such as by lowering it from a contact angle between 40 and 60°, for example, immediately after dripping pure water on this layer, to between 5 and 20° after 5 minutes. In other words, the degree of hydrophilicity can be changed according to elapse of time.

By changing the contact angle over a sufficiently wide range as described, a wide range of contact angles with pure water is available. Also, the substrate must be designed so that its contact angle with pure water will change significantly over a short period of time.

The value of change in the contact angle of the base material with pure water is preferably 15° or greater, or preferably 20° or greater, representing the difference between the value of immediate contact angle and the value of contact angle after 5 minutes.

Coating a cosmetic preparation on such surface whose contact angle changes significantly causes the stability of coating film (that is, uniformity of coating film) of the cosmetic preparation to also change according to the change (decrease) in the contact angle after coating. When the most uniform coating film possible with the cosmetic preparation can be formed at a contact angle at a given point in time during the course of this change in contact angle, the coating film is fixed in the most uniform and stable state. The result is that phase separation no longer occurs between the aqueous phase and the oil phase, etc., in the coating film, and that the coating film no longer falls into a state where it is repelled from parts of the substrate surface (state where parts of the coating film are repelled, and holes are created). Accordingly, the uniform layer can be measured with higher precision, while also stabilizing in a state that allows for measurement of high absorbance.

In other words, any cosmetic preparation that can form a uniform coating film on a surface whose contact angle with pure water is in a range of 5 to 60°, permits accurate measurement of SPF value using the substrate for UV transmittance evaluation proposed by the present invention.

The coating weight of the compound that has a sugar skeleton but is not a salt is not limited in any way; however, preferably it is coated by 2 to 15 mg per 100 $cm^2$ of base material.

Compounds that may be applied on the hydrophilized base material surface to cause the contact angle to change significantly as described above, include the following compounds that have a sugar skeleton but are not salts. Among these compounds, one or more types selected from mannose, galactose, xylose, glucose, maltose, lactose, sucrose, trehalose, fructose, cellulose, hydroxyethyl cellulose, hydroxypropyl cellulose, carboxymethyl cellulose, and other cellulose derivatives, maltotriose, raffinose, and other trisaccharides, inulin and other tetrasaccharides, oligosaccharide, glucan, agar, α-cyclodextrin, maltodextrin, cornstarch, powdered arrowroot, tapioca starch, potato starch, flour starch, hydroxyethyl starch, hydroxypropyl starch, Tamarind gum, xanthan gum, native gellan gum, gellan gum, and other compounds having a sugar skeleton, which are solubilized as necessary, may be used. For example, cellulose derivatives are preferred.

These compounds share a common property of changing the substrate's contact angle with pure water after treatment, and are each associated with a different range over which the contact angle will change. Also, one type of compound may be selected from these compounds and used, or multiple types may be selected and used in combination. In cases where selecting and using only one type of compound fails to achieve a desired range of contact angle change for the cosmetic preparation being the test subject, multiple compounds may be combined to adjust the range of contact angle change.

However, compounds that are insoluble in water, or compounds that have a sugar skeleton but are not salts, cannot be used alone under the present invention because forming their layers on a quartz plate will not change the contact angle with pure water in any particular way.

It should be noted that erythritol, xylitol, and other sugar alcohols, sugar-derived compounds, and other non-sugar compounds may or may not be compounded to the extent that the effects of the present invention are not impaired.

Furthermore, in the sense that they are to constitute a layer, preferably these compounds are solid at normal temperature and pressure, have no deliquescence, and are not insoluble in water at room temperature. "Not insoluble" means having a solubility of 1 g/100 mL of water at room temperature or higher. Additionally, compounds having a solubility of 5 g/100 mL or higher are more preferred.

However, containing any compound that is a salt having a sugar skeleton makes it difficult to sufficiently change the water contact angle, and therefore such compound will not be contained. Also, cellulose triacetate is insoluble in water and therefore will not be used.

The method for forming a layer containing a compound that has a sugar skeleton but is not a salt is not limited in any way, and any method will do so long as it can form such layer uniformly.

To be specific, a coating solution of the aforementioned compound that has a sugar skeleton but is not a salt, is coated on the aforementioned hydrophilized plate or sheet. Solvents for the coating solution include water, lower alcohols, and other volatile solvents, where distilled water is particularly preferred and mixed solvents constituted by distilled water and lower alcohols are also preferred.

To prevent the coating solution from running off the plate or sheet during coating, preferably a hydrophobic masking tape is attached along the borders of the surface of the plate or sheet to create a frame beforehand, and the coating solution is coated inside this frame. For the masking tape, commercial plastic tapes and polyimide tapes are preferred due to excellent handling. The tape also has the benefit of preventing such plates or sheets from adhering to each other when stacked in the next packing process.

Next, the coating solution layer formed on the plate or sheet surface is dried. Drying methods include heat drying, freeze drying, decompression drying, and other methods. It should be noted that preferably the coating solution is prevented from becoming nonuniform during drying. Preferably the drying temperature is in a range of 40 to 120° C.

(Storage)

Once a layer containing a compound that has a sugar skeleton but is not a salt is formed on the base material as described above, it must be stored in a plastic bag or other sealed container together with a drying agent, so that the compound in the aforementioned layer will not absorb moisture and crystallize, etc., during storage.

Next, the measurement method proposed by the present invention is presented.

A cosmetic preparation is coated on a substrate for UV transmittance evaluation obtained as described above, a UV absorption measuring system is used to measure the UV absorption spectrum of its dried coating film as absorbance, and based on the measured result, a measured SPF value is obtained.

The means for applying the cosmetic preparation on the surface of the aforementioned substrate is not limited in any way, and any means will do so long as it permits uniform application. For example, the means under the method below for measuring the UV protection effect of a liquid cosmetic preparation may be adopted.

Method for measuring the UV protection effect of a liquid cosmetic preparation through steps a) to d) below:
  a) A step to apply a liquid cosmetic preparation on a base material and then move, preferably at a constant speed (1 to 10 mm/s), a spreading member which is a metal four-way applicator with gaps ranging from 5 to 25 μm, to coat/form a smooth liquid cosmetic preparation layer on the substrate.
  b) A step to measure the film thickness of the coating film immediately after coating, using a wet film thickness gauge.
  c) A step to measure the absorbance of the coating film using an SPF analyzer.
  d) A step to obtain the SPF value and UVA-PF value at the reference film thickness based on the film thickness obtained in b).

For the applicator used in step a), one having gaps of 5 to 25 μm from the substrate is used. In terms of the measurement sensitivity of the SPF analyzer, the thinner the film thickness, the better; if, however, particles of sizes exceeding 5 μm are compounded in the cosmetic preparation, they may lodge in the gaps, and lines may be drawn as the applicator is moved, resulting in failed coating. This is why, for a general cosmetic preparation, an applicator with gaps ranging from 10 to 15 μm is particularly preferred.

The wet film thickness gauge used in step b) may be of rotary type or edge type, where a rotary-type gauge conforming to the provisions of JIS K5600-1-7 is preferred and one having a measurement range of 0 to 25 μm is preferred.

The SPF analyzer used in step c) may be SPF-290AS manufactured by U.S.-based Solar Light Company (https://solarlight.com/product/spf-290as-spf-analyzer/), for example. When computing the measured value, the SPF V.30 software that comes with Solar Light's SPF-290AS or other UV protection effect calculation program currently studied in each geographical region can be used for SPF and UVA-PF calculations.

The reference film thickness in step d) may be, for example, 20 μm corresponding to a coating weight of 2 mg/cm$^2$ currently used in in-vivo measurements, or any of values ranging from 5 to 10 μm reportedly representing weights being coated by consumers in practice.

In the meantime, cosmetic preparations are constituted by mixtures of many components, and determining their wetting property based solely on the mixture composition is difficult. Accordingly, in the case of cosmetic preparations that form a coating film demonstrating the highest UV protection effect on a surface whose contact angle with pure water is 5 to 60°, their SPF value can be measured using the substrate for UV transmittance evaluation proposed by the present invention.

In the case, however, of cosmetic preparations that form a uniform coating film on a surface having a contact angle with pure water outside a range of 5 to 60°, a superhydrophilized substrate obtained by corona-discharge-treating a quartz plate, or UV-transmitting PMMA (polymethyl methacrylate) plate with a water contact angle of 60° or greater, will be used, instead of the surface of the substrate for UV transmittance evaluation proposed by the present invention, to coat each such liquid cosmetic preparation according to the above methods a) to d) and evaluate the UV protection effect of the cosmetic preparation using the measured result on the substrate representing the highest of the obtained measured values.

EXAMPLES

The present invention is explained in greater detail below using examples; it should be noted, however, that the present invention is not limited to these examples.

(A. Confirmation of Change in Contact Angle on Surface of Substrate for UV Transmittance Evaluation)

(Method for Measuring Contact Angle)

For measurement of contact angle, 3.1 μL of distilled water was dripped, using a contact angle measuring system (SImage Entry 5, manufactured by Excimer Inc.), onto a sample being the surface of the substrate for UV transmittance evaluation, and its contact angle was measured immediately thereafter and also after an elapse of 5 minutes. The difference between the measured values obtained by these two contact angle measurements was taken as the difference in contact angle.

(How to Obtain SPF and UVA-PF)

SPF and UVA-PF were obtained using the SPF V3.0 software that came with Solar Light's SPF-290AS. Film thickness conversions and corrections by application weight were obtained by calculations.

Example 1

The periphery of a corona-discharge-treated quartz plate (10-cm square, 0° contact angle with pure water) was framed with a polyimide tape of 3 mm in width. Next, a coating solution (aqueous solution containing hydroxyethyl cellulose which is a type of cellulose derivative) was coated inside the tape until the coating weight of hydroxyethyl cellulose became 7 mg per 100 $cm^2$ of base material, after which the quartz plate was dried under heating, to prepare a substrate for UV transmittance evaluation.

It should be noted that a quartz plate to which only corona discharge treatment has been given, has a property of undergoing a rise in the contact angle of its surface over time following the corona discharge treatment.

Example 2

A substrate for UV transmittance evaluation was prepared in the exact same manner as in Example 1, except that hydroxypropyl cellulose, instead of hydroxyethyl cellulose in Example 1, was coated to 3 mg per 100 $cm^2$ of base material.

Example 3

A substrate for UV transmittance evaluation was prepared in the exact same manner as in Example 1, except that a mixture of 5 mg of hydroxyethyl cellulose and 5 mg of raffinose, instead of hydroxyethyl cellulose in Example 1, was coated to a total of 10 mg per 100 $cm^2$ of base material.

Example 4

A substrate for UV transmittance evaluation was prepared in the exact same manner as in Example 1, except that agar, instead of hydroxyethyl cellulose in Example 1, was coated to 10 mg per 100 $cm^2$ of base material.

Example 5

A substrate for UV transmittance evaluation was prepared in the exact same manner as in Example 1, except that xanthan gum, instead of hydroxyethyl cellulose in Example 1, was coated to 5 mg per 100 $cm^2$ of base material.

Example 6

A substrate for UV transmittance evaluation was prepared in the exact same manner as in Example 1, except that native gellan gum, instead of hydroxyethyl cellulose in Example 1, was coated to 5 mg per 100 $cm^2$ of base material.

Example 7

A substrate for UV transmittance evaluation was prepared in the exact same manner as in Example 1, except that a mixture containing xanthan gum and glucose at a ratio by weight of 2:1, instead of hydroxyethyl cellulose in Example 1, was coated to 5 mg per 100 $cm^2$ of base material.

Example 8

A substrate for UV transmittance evaluation was prepared in the exact same manner as in Example 1, except that a mixture containing native gellan gum and α-cyclodextrin at a ratio by weight of 5:1, instead of hydroxyethyl cellulose in Example 1, was coated to 5 mg per 100 $cm^2$ of base material.

Comparative Example 1

A substrate for UV transmittance evaluation was prepared in the exact same manner as in Example 1, except that glycerin, instead of hydroxyethyl cellulose in Example 1, was coated to 10 mg per 100 $cm^2$ of base material.

Comparative Example 2

A substrate for UV transmittance evaluation was prepared in the exact same manner as in Example 1, except that erythritol, instead of hydroxyethyl cellulose in Example 1, was used.

Comparative Example 3

A substrate for UV transmittance evaluation was prepared in the exact same manner as in Example 1, except that sodium carboxymethyl cellulose, instead of hydroxyethyl cellulose in Example 1, was used.

Comparative Example 4

A substrate for UV transmittance evaluation was prepared in the exact same manner as in Example 1, except that xylitol, instead of hydroxyethyl cellulose in Example 1, was coated to 10 mg per 100 $cm^2$ of base material.

Evaluation of Examples and Comparative Examples

The substrates for UV transmittance evaluation conforming to the present invention were evaluated for whether or not the contact angle with pure water had changed by 15 degrees or more within 5 minutes. If the difference in contact angle is under 15 degrees, stable measurement may not be possible when a cosmetic preparation is applied on the substrate, depending on the formulation of the cosmetic preparation. The results are shown in Table 1.

According to the Examples, the difference in contact angle was 15 degrees or more in all cases. However, it was 3.8 degrees in Comparative Example 1, 0.8 degrees in Comparative Example 2, 8.5 degrees in Comparative Example 3, and 3.5 degrees in Comparative Example 4.

TABLE 1

|  | Difference in contact angle is 15 degrees or more |
| --- | --- |
| Example 1 | Applicable |
| Example 2 | Applicable |
| Example 3 | Applicable |
| Example 4 | Applicable |
| Example 5 | Applicable |
| Example 6 | Applicable |
| Example 7 | Applicable |
| Example 8 | Applicable |
| Comparative Example 1 | Not applicable |

TABLE 1-continued

| | Difference in contact angle is 15 degrees or more |
|---|---|
| Comparative Example 2 | Not applicable |
| Comparative Example 3 | Not applicable |
| Comparative Example 4 | Not applicable |

Based on the results in Table 1, all of the Examples conforming to the present invention exhibited a property of the contact angle changing over a short period of time, while the contact angle either did not change or changed only slightly in all of the Comparative Examples. This means that, under Comparative Examples 1 to 4 that used a compound being a salt or not having a sugar skeleton and consequently produced a small difference in contact angle, many such substrates must be used whose surface tension (contact angle) changes over a narrow range, in order to find a substrate having an optimal contact angle for each cosmetic preparation. According to Examples 1 to 8, where the contact angle on the substrate surface changes significantly over time after application of a cosmetic preparation, each such substrate allows measurement of SPF value to be completed through a single application/measurement on the substrate, which is one of the objects of the present invention.

In light of the compounds used in the aforementioned examples, it is understood that, under the present invention, various sugars ranging from monosaccharides to polysaccharides may be used, to the extent that they are not insoluble in water, so long as they share a common aspect of having a sugar skeleton and are each a compound that is not a salt.

(Cosmetic Preparations Used in Example 9 (Cosmetic Preparations 1 to 8))

(Cosmetic Preparation 1)

Purified water, ethylhexyl methoxycinnamate, BG, diethylamino-hydroxybenzoyl hexyl benzoate, ethanol, ethylhexyl triazone, bis-ethylhexyloxyphenol methoxyphenyl triazine, dimethicone, diisopropyl adipate, methyl methacrylate crosspolymer, (HDI/trimethylol hexyllactone) crosspolymer, PEG-20 glyceryl triisostearate, ethylhexyl glycerin, glyceryl caprylate, sorbitan sesquiisostearate, (acrylates/beheneth-25 methacrylate) copolymer, potassium hydroxide (Cosmetic Preparation 2)

Water, ethanol, ethylhexyl methoxycinnamate, dimethicone, diisopropyl sebacate, ethylhexyl triazone, bis-ethylhexyloxyphenol methoxyphenyl triazine, diethylamino-hydroxybenzoyl hexyl benzoate, (HDI/trimethylol hexyllactone) crosspolymer, titanium oxide, glycerin, oxybenzone-3, caprylyl methicone, (acrylates/methoxy PEG-90 methacrylate) crosspolymer, PEG/PPG-14/7 dimethyl ether, xanthan gum, lauryl betaine, tea extract, cherry leaf extract, *Rosa canina* fruit extract, sodium acetyl hyaluronate, tormentilla root extract, aloe vera leaf extract, water-soluble collagen, PPG-17, (palmitate/ethylhexanoate) dextrin, dextrin palmitate, hydrous silica, triethoxycaprylylsilane, carbomer, agar, potassium hydroxide, (acrylates/alkyl acrylate (C10-30)) crosspolymer, silica, distearyldimonium chloride, BG, stearic acid, BHT, phenoxy ethanol, sodium benzoate, aromatic chemicals (Cosmetic Preparation 3)

Water, cyclomethicone, talc, BG, octyl methoxycinnamate, dimethicone, isostearic acid, PEG/PPG-14/7 dimethyl ether, tocopherol acetate, sodium hyaluronate, water-soluble collagen, aluminum distearate, dimethicone copolyol, aluminum hydroxide, calcium stearate, distearyldimonium hectorite, glycerin, trisodium EDTA, triethoxycaprylylsilane, BHT, tetrahydrotetramethyl cyclotetrasiloxane, tetradecene, tocopherol, phenoxy ethanol, methylparaben, (+/−) titanium oxide, mica, iron oxide, cobalt titanate (Cosmetic Preparation 4)

Placenta extract, dipotassium glycyrrhizate, water, concentrated glycerin, BG, 2-ethylhexyl paramethoxycinnamate, polyoxyethylene hardened castor oil, dipropylene glycol, ethanol, placenta extract (1), L-cysteine, yellowtail elastin, collagen, tripeptide F sodium hyaluronate (2), yuzu ceramide, stearoyloxyheptacosanoyl phytosphingosine, N-stearoyl dihydrosphingosine, N-stearoyl phytosphingosine, hydroxystearyl phytosphingosine, artichoke extract, liquid cherry leaf extract, prune-enzyme decomposition product, raspberry extract, yeast extract (3), snow fungus polysaccharide, brown sugar, trimethyl glycine, cetyl 2-ethyl hexanoate, di(phytosteryl-2-octyldodecyl) N-lauroyl-L-glutamate, phytosterol, natural vitamin E, 4-tert-butyl-4'-methoxydibenzoylmethane, xanthan gum, carboxyvinyl polymer, potassium hydroxide, sodium citrate, disodium edetate, hydrogenated soybean phospholipid, methylparaben, phenoxyethanol (Cosmetic Preparation 5)

Water, cyclopentasiloxane, methyl methacrylate crosspolymer, titanium oxide, ethanol, ethylhexyl methoxycinnamate, PEG-10 dimethicone, glycerin, DPG, cetyl ethylhexanoate, distearyldimonium hectorite, diphenylsiloxy phenyl trimethicone, aloe vera leaf extract, chestnut rose extract, PEG-9 polydimethylsiloxyethyl dimethicone, isostearic acid, trisodium EDTA, aluminum hydroxide, stearic acid, alumina, triethoxycaprylylsilane, silica, tetrahydro-tetramethylcyclotetrasiloxane, BG, BHT, tetradecene, tocopherol, rosemary leaf extract, phenoxyethanol, methylparaben, iron oxide, barium sulfate (Cosmetic Preparation 6)

Water, cyclopentasiloxane, ethanol, ethylhexyl methoxycinnamate, hydrogenated polyisobutene, zinc oxide, (vinyl dimethicone/methicone silsesquioxane) crosspolymer, octocrylene, DPG, polylmethylsilsesquioxane, polysilicone-15, PEG-9 polydimethylsiloxyethyl dimethicone, di ethylamino-hydroxybenzoyl hexyl benzoate, sodium hyaluronate, tocopherol acetate, tocopherol, polyglyceryl-3 diisostearate, triethoxysilylethyl polydimethylsiloxyethyl hexyl dimethicone, sodium chloride, BHT, disodium EDTA, methylparaben, propyl paraben (Cosmetic Preparation 7)

Water, ethylhexyl methoxycinnamate, DPG, diethylamino-hydroxybenzoyl hexyl benzoate, dimethicone, glycerin, polymethyl silsesquioxane, ethanol, isostearic acid, sodium hyaluronate, water-soluble collagen, ceramide NP, peach leaf extract, capillary *artemisia* flower extract, aloe *arborescens* leaf extract, licorice root extract, tocopherol acetate, potassium hydroxide, (acrylates/alkyl acrylate (C10-30)) crosspolymer, PEG-9 polydimethylsiloxyethyl dimethicone, tocopherol, xanthan gum, BG, phenoxyethanol, methylparaben (Cosmetic Preparation 8)

Dimethicone, water, zinc oxide, ethanol, ethylhexyl methoxycinnamate, talc, isopropyl myristate, methyl methacrylate crosspolymer, cyclopentasiloxane, isododecane, octocrylene, titanium oxide, PEG-9 polydimethylsiloxyethyl dimethicone, diethylamino-hydroxybenzoyl hexyl benzoate, glycerin, diisopropyl sebacate, (vinyl dimethicone/methicone silsesquioxane) crosspolymer, silica, dextrin palmitate, xylitol, trimethyl siloxysilicate, bis-ethylhexyloxyphenol methoxyphenyl triazine, PEG/PPG-14/7 dimethyl ether, sodium chloride, tea extract, cherry leaf extract, *Rosa canina* fruit extract, sodium acetyl hyaluronate, tormentilla root extract, aloe vera leaf extract, water-soluble collagen, PPG-17, triethoxycaprylylsilane, isostearic acid, distearyldimonium chloride, distearyldimonium hectorite, aluminum hydroxide, stearic acid, trisodium EDTA, BHT, tocopherol, isopropanol, BG, sodium pyrosulfite, phenoxyethanol, aromatic chemicals Example 9

(B. Confirmation of Change in Measured SPF Value Relative to Contact Angle on Base Material Surface, and Peak Value)

Multiple quartz plates, each having a different contact angle, were prepared by changing the contact angles of corona-discharge-treated quartz plates having no layer containing a compound that has a sugar skeleton but is not a salt, by means of adjusting the elapsed time after corona discharge treatment. FIG. 1 shows the relationship between the contact angle and the SPF value obtained from each of these quartz plates when Cosmetic Preparation 1 was coated thereon under the conditions below. The horizontal axis represents contact angle with pure water, while the vertical axis represents SPF value. According to FIG. 1, clearly the SPF value changes dependent on the contact angle of the substrate.

(Measurement Method)

Testing was conducted after the masking tape along the periphery of the substrate was peeled prior to measurement. Using a stainless-steel four-way applicator with a gap of 10 μm, a smooth liquid cosmetic preparation layer was formed on the substrate by moving the applicator at a speed of 5 mm/s. Immediately after a coating layer was formed, the film thickness was measured using a rotary-type wet film thickness gauge, followed by absorbance measurement of the coating film using an SPF analyzer (SPF-290AS, manufactured by Solar Light Company). Everything was done at room temperature.

The vertical axis in FIG. 1 represents SPF value, while the horizontal axis represents contact angle.

From FIG. 1, clearly Cosmetic Preparation 1 has a peak of SPF value at a contact angle with pure water near 30 to 40°, especially near 30°. Also, the surfaces of cosmetic preparation coating films obtained by having coated the sample on the substrates whose contact angle was not near 30 to 40°, were not uniform and exhibited a state of minute phase separation or nonuniform morphology likely caused by the sample being repelled from parts of the substrate surface. When the coating film surface takes on a nonuniform morphology, more UV rays transmit through the areas where the coating film is thinner or areas representing holes, and therefore the SPF value tends to become lower, while a uniform coating film tends to produce a higher measured value.

(C. Measurement of SPF Value Using Substrate for UV Transmittance Evaluation Proposed by Present Invention)

On the substrate prepared in Example 1, Cosmetic Preparation 1 above was applied to form a coating film using the aforementioned stainless-steel four-way applicator in the same manner as in B above, and the change in SPF value was measured based on the manner used in B above. As a result, as shown in Table 2, the measured SPF peak value of the sunscreen was 30.5 (average value of 3 measurements), roughly matching the peak value in FIG. 1.

According to the measurement methods and measured values per B and C, the substrate for UV transmittance evaluation proposed by the present invention provides an effect of requiring only one type of substrate in finding a substrate for SPF measurement having a contact angle that permits uniform application of a cosmetic preparation.

In addition to this effect, an effect of making one type of substrate sufficient for use in measuring the SPF value of a cosmetic preparation, as well as an effect of reducing to one the number of substrates used for finding a substrate meeting the required range of surface tensions (contact angles) specific to a cosmetic preparation, while also permitting accurate measurement of SPF value based on a single application of a cosmetic preparation on a substrate, can be achieved.

(D. Measurement of SPF Value with Different Sunscreens)

The SPF value was measured in the same manner as the measurement method in C above, except that the sunscreen was changed to each of Cosmetic Preparations 2 to 8 above.

With these different sunscreens, the average values of measured SPF based on 3 measurements are shown in Table 2 below.

The cosmetic preparations, even though they each have a different SPF value, could be measured for SPF value using one type of substrate for UV transmittance evaluation. Also, the coating films of the cosmetic preparations were uniform and not in a state of phase separation or being repelled from parts of the substrate surface.

The cosmetic preparations are of different types and thus base materials on which they can be applied uniformly have different values of contact angle with water in normal circumstances. Despite the cosmetic preparations requiring different values of contact angle for base materials on which they can be applied uniformly, as described above, their coating films did not undergo phase separation and were not repelled from parts of the substrate surface, which indicates that all of the cosmetic preparations could be applied uniformly on the substrate for UV transmittance evaluation proposed by the present invention. This also indicates that SPF values were measured accurately. Also, use of the substrate for UV transmittance evaluation proposed by the present invention allowed uniform coating films of the cosmetic preparations to be present in a stable manner following the application.

TABLE 2

| | Type | SPF | UVA-PF | State of phase separation or being repelled from parts of substrate surface |
|---|---|---|---|---|
| Cosmetic Preparation 1 | Skin milk | 30.5 | | |
| Cosmetic Preparation 2 | Gel-type sunscreen | 22.8 | 7.6 | None |
| Cosmetic Preparation 3 | Makeup base | 4.1 | 1.8 | None |
| Cosmetic Preparation 4 | Lotion | 2.2 | 1.2 | None |
| Cosmetic Preparation 5 | Foundation | 3.4 | 1.9 | None |
| Cosmetic Preparation 6 | W/O-type sunscreen | 6.5 | 2.6 | None |
| Cosmetic Preparation 7 | Cream | 28.8 | 12.2 | None |
| Cosmetic Preparation 8 | Skin milk | 17.5 | 5.8 | None |

According to the substrate for UV transmittance evaluation proposed by the present invention, many different types of cosmetic preparations can be measured, each using a single substrate for UV transmittance evaluation, as shown in Table 2 above.

Among these, Cosmetic Preparations 3 and 8 were measured for SPF value and UVA-PF value using multiple measurement substrates having varying contact angles with water that were adjusted and changed by corona-discharge treatment and through a subsequent elapse of time, with no layer provided thereon that contained a compound that has a sugar skeleton but is not a salt.

The relationships between the values of contact angle of the respective substrates, and the measured SPF values, are shown in FIG. 2 and FIG. 3. The horizontal axes of the graphs represent contact angle, while the vertical axes of the graphs represent Sun Protection Factor. Both graphs show a convex waveform, where the peak SPF values matched well the measured values shown in Table 2, above, obtained using the substrate for UV transmittance evaluation proposed by the present invention.

The results shown in FIGS. 2 and 3 each indicate that, when conventional substrates whose contact angle with pure water takes a specific value are used, obtaining an appropriate contact angle for accurately measuring the change in SPF value requires three or more types of substrates.

By contrast, the substrate for UV transmittance evaluation proposed by the present invention permits measurement of the SPF value of a cosmetic preparation using a single substrate of a single type.

An example of measuring Cosmetic Preparation 4 over a wide range of contact angles is shown in FIG. 4. The descriptions of the axes are the same as above. In a range of contact angles from 5 to 55°, the peak value of SPF matched the measured value shown in Table 2 obtained using the substrate proposed by the present invention.

However, a higher value (4.4) was indicated in a super-hydrophilic state at a contact angle of 0°. Additionally, a high value (2.4) was also indicated in a high water-repellent state at a contact angle of approx. 70°.

As described above, cosmetic preparations that can form a uniform coating film due to the contact angle being in a range of 5 to 60°, can be measured for SPF value using the substrate for UV transmittance evaluation proposed by the present invention. Moreover, besides the cosmetic preparations having the compositions corresponding to Cosmetic Preparations 1 to 8 above, cosmetic preparations having different compositions can also be measured accurately using the substrate for UV transmittance evaluation proposed by the present invention, so long as such cosmetic preparations can form a uniform coating film when the contact angle is 5 to 60°.

Furthermore, regarding cosmetic preparations that are not clear as to the levels of contact angles with pure water on substrates where they can form a uniform coating film, they may be measured using the substrate for UV transmittance evaluation proposed by the present invention, followed, if necessary, by a combined use of super-hydrophilic substrates and PMMA substrates having high contact angles with pure water, to evaluate in which region of contact angles they exhibit the highest SPF value.

Example 10

(E. Effectiveness Evaluation of Wet Film Thickness Gauge)

Using the substrate in Example 1, as well as the model sunscreen and coating method used in the effectiveness evaluation of substrates for UV transmittance evaluation, the film thickness was measured to an accuracy of 1 μm using a rotary-type wet film thickness gauge immediately after coating. The obtained absorbance curve was converted to the unit film thickness (5 μm), and equivalent SPF and UVA-PF values were obtained using the SPF V3.0 software that came with Solar Light's SPF-290AS. Measurement was performed three times.

Comparative Example 5

Three measurements were performed in the same manner as in Example 10, except that the film thickness was measured to an accuracy of 0.1 μm using Keyence's laser displacement gauge (LT-9010M+LT-9500) instead of the rotary-type wet film thickness gauge used in Example 10. For the laser displacement gauge, a reference point of measurement was set beforehand using a permanent marker, and an equivalent film thickness was calculated from the measured values taken near the reference point before and after coating, and used.

Table 3 shows the measured results of Example 10 and Comparative Example 5. The three measured values are listed in order for Example 10 and Comparative Example 5, respectively. The coating film of cosmetic preparation obtained in Example 10 was still uniform 2 days later.

TABLE 3

|  | SPF value | UVA-PF value |
| --- | --- | --- |
| Example 10 (1st measurement) | 5.13 | 2.39 |
| Example 10 (2nd measurement) | 6.97 | 3 |
| Example 10 (3rd measurement) | 6.72 | 2.88 |
| Comparative Example 5 (1st measurement) | 116.46 | 54.3 |
| Comparative Example 5 (2nd measurement) | 550.39 | 184922 |
| Comparative Example 5 (3rd measurement) | 223.13 | 358.85 |

From the results in Table 3, the three measured values in the Example were roughly comparative and stable, and largely close to the design value. Also, the coating film was stable and uniform. By contrast, the measured values in the Comparative Example were excessive, and the three measured values varied significantly. This is probably because, while the wet film thickness gauge was able to perform quick measurement immediately after coating when the sunscreen was not yet dry, the optical measurement took some time to measure and therefore, even though it produced measured values that were apparently precise, the coating film dried during measurement and thus the film thickness decreased, causing the measured values by calculation to increase. Based on these results, clearly the method using a wet film thickness gauge capable of obtaining measured results that are closer to reality presents an accurate and utterly superior method of correction when measuring thin films of sunscreens.

What is claimed is:

1. A substrate for UV transmittance evaluation, comprising a base material that allows UV rays in a range of 290 to 400 nm to transmit through, and a layer provided on one side thereof that contains at least one compound, other than cellulose triacetate, which has a sugar skeleton but is not a salt, wherein a surface of the layer has a contact angle change property which is defined as a change in contact angle with distilled water 5 minutes after dripping the water onto the layer that contains at least one compound, other than cellulose triacetate, which has a sugar skeleton but is not a salt, said change being at least 15 degrees as compared with a contact angle immediately after the dripping of the water.

2. The substrate for UV transmittance evaluation according to claim 1, wherein the base material that allows UV rays in a range of 290 to 400 nm to transmit through is a quartz plate.

3. The substrate for UV transmittance evaluation according to claim 2, wherein the compound that has a sugar skeleton but is not a salt is at least one type selected from mannose, galactose, xylose, glucose, maltose, lactose, sucrose, trehalose, fructose, cellulose, hydroxyethyl cellulose, hydroxypropyl cellulose, carboxymethyl cellulose, maltotriose, raffinose, inulin, oligosaccharide, glucan, agar, α-cyclodextrin, maltodextrin, cornstarch, powdered arrowroot, tapioca starch, potato starch, flour starch, hydroxyethyl starch, hydroxypropyl starch, Tamarind gum, xanthan gum, native gellan gum, and gellan gum.

4. A measurement method for SPF value, comprising steps A and B below:
　A. coating a cosmetic preparation on the layer provided on the one side of the substrate for UV transmittance evaluation according to claim 2; and
　B. measuring an UV absorption spectrum that transmits through a coated substrate for UV transmittance evaluation, to obtain a transmittance and also obtain an SPF value.

5. The substrate for UV transmittance evaluation according to claim 1, wherein the compound that has a sugar skeleton but is not a salt is at least one type selected from mannose, galactose, xylose, glucose, maltose, lactose, sucrose, trehalose, fructose, cellulose, hydroxyethyl cellulose, hydroxypropyl cellulose, carboxymethyl cellulose, maltotriose, raffinose, inulin, oligosaccharide, glucan, agar, α-cyclodextrin, maltodextrin, cornstarch, powdered arrowroot, tapioca starch, potato starch, flour starch, hydroxyethyl starch, hydroxypropyl starch, Tamarind gum, xanthan gum, native gellan gum, and gellan gum.

6. A measurement method for SPF value, comprising steps A and B below:
　A. coating a cosmetic preparation on the layer provided on the one side of the substrate for UV transmittance evaluation according to claim 4; and
　B. measuring an UV absorption spectrum that transmits through a coated substrate for UV transmittance evaluation, to obtain a transmittance and also obtain an SPF value.

7. A measurement method for SPF value, comprising steps A and B below:
　A. coating a cosmetic preparation on the layer provided on the one side of the substrate for UV transmittance evaluation according to claim 1; and
　B. measuring an UV absorption spectrum that transmits through a coated substrate for UV transmittance evaluation, to obtain a transmittance and also obtain an SPF value.

8. A measurement method for SPF value, comprising steps A and B below:
　A. coating a cosmetic preparation on the layer provided on the one side of the substrate for UV transmittance evaluation according to claim 3; and
　B. measuring an UV absorption spectrum that transmits through a coated substrate for UV transmittance evaluation, to obtain a transmittance and also obtain an SPF value.

* * * * *